United States Patent [19]

Nathanielsz

[11] Patent Number: 5,217,022

[45] Date of Patent: Jun. 8, 1993

[54] ELECTRICAL IMPEDANCE IMAGING TO MONITOR MYOMETRIAL ACTIVITY

[75] Inventor: Peter W. Nathanielsz, Ithaca, N.Y.

[73] Assignee: Cornell Research Foundation, Inc., Ithaca, N.Y.

[21] Appl. No.: 798,902

[22] Filed: Nov. 27, 1991

[51] Int. Cl.$^5$ .............................................. A61B 5/05
[52] U.S. Cl. ................................... 128/734; 128/693; 128/778
[58] Field of Search ............... 128/734, 738, 778, 774, 128/693, 733, 660.06, 660.07, 661.07, 775

[56] References Cited

U.S. PATENT DOCUMENTS

| | | | |
|---|---|---|---|
| 4,263,920 | 4/1981 | Tasto et al. | 128/734 |
| 4,486,835 | 12/1984 | Bai et al. | 364/414 |
| 4,539,640 | 9/1985 | Fry et al. | 364/414 |
| 4,577,640 | 3/1986 | Hofmeister | 128/738 |
| 4,617,939 | 10/1986 | Brown et al. | 128/734 |
| 4,967,761 | 11/1990 | Nathanielsz | 128/733 |
| 5,042,503 | 8/1991 | Török et al. | 128/775 |
| 5,070,888 | 12/1991 | Hon et al. | 128/778 |

FOREIGN PATENT DOCUMENTS 278014 10/1970 U.S.S.R. .............. 128/734
2119520 11/1983 United Kingdom .

OTHER PUBLICATIONS

Nathanielsz, P. W., et al., 1984, Methods for investigation of the chronically instrumented pregnant rhesus monkey preparation maintained on a tether and swivel system, In Animal Models in Fetal Medicine, p. W. Nathanielsz, editor, Perinatology Press, 109–160.

Smyth, C. N., 1957, The guard-ring tocodynamometer; Absolute Measurement of intra-amniotic pressure by a new instrument, J. Obstet. Gynaecol. Brit. Empire 64(1):59–66.

Brown, B. H., 1985, Applied potential tomography: possible clinical applications, Clin. Phys. Physiol. Meas. 6:109–121.

Main, D. M., et al., 1990, The use of a pulsatile oxytocin (OT) challenge test to determine variation in myometrial response to OT at different times of day in the human at 30 to 40 weeks gestation, Society for Gynecological Investigation, Abstract No. 395.

Figueroa, J. P., et al., 1989, Effect of 48 hour intravenous 4A androstenedione infusion on the pregnant rhesus monkey in the last third of gestation: changes in maternal plasma estradiol concentrations and myometrial contractility, Am. J. Obstet. Gynecol. 161:481–486.

Sunderji, S. G., et al., 1984, The effect of myometrial contractures on uterine blood flow in the pregnant sheep at 114–140 days gestation measured by the 4 amino antipyrine equilibrium diffusion technique, Am. J. Obstet. Gynecol. 149:408–412.

Randall, N. J., et al., 1988, Validation of thermal techniques to measure pelvic organ blood flows in the ovarieatomized non-pregnant sheep: Comparison with transit time ultrasonic and microsphere measurements of blood flow, Am. J. Obstet. Gynecol. 158:651–658.

Honnebier, M. B. O. M., et al., 1989, Variation in myometrial response to pulsatile intravenous oxytocin administration–a pulsatile oxytocin challenge test at different times of the day in the pregnant at 121 to 138 days gestational age, Endocrinology 125:1498–1503.

Morgan, M., et al., 1990, Power spectral analysis (PSA) of myometrial electromyogram (EMG) acdtivity in late gestation pregnant baboon, Society for Gynecologic Investigation, Abstract No. 141.

Taylor, N. F., et al., 1983, The fetus determines circadian oscillation of myometrial electromyographic activity in the pregnant rhesus monkey, Am. J. Obstet. Gynecol. 146:557–567.

(List continued on next page.)

Primary Examiner—Max Hindenburg
Assistant Examiner—Guy V. Tucker
Attorney, Agent, or Firm—Jones, Tullar & Cooper

[57] ABSTRACT

A non-invasive technique for monitoring myometrial activity in pregnant females employs electrical impedance imaging (EII) to obtain periodic measurements of the integrated resistivity of a pregnant female's abdomen. The integrated resistivity has been shown experimentally to be directly related to myometrial activity, particularly uterine contractility.

3 Claims, 2 Drawing Sheets

OTHER PUBLICATIONS

Figueroa, J. P., et al., 1985, Characteristics and analysis of uterine electromyographic activity in the pregnant sheep, *Am. J. Obstet. Gynecol.* 151:524–531.

Hsu, H. W., et al., 1989, Power spectrum analysis of myometrial electromyogram and intrauterine pressure changes in the pregnant rhesus monkey in late gestation, *Am. J. Obstet. Gynecol.* 161:467–473.

Binienda, Z., et al., 1988, The effect of food withdrawal of arterial blood glucose and plasma 13,14 dihydro-1-5-keto-prostaglandin . . . , *Am. J. Obstet. Gynecol.* 160:746–750.

Harbert, Jr., M. D., Guy M., *Am. J. Obstet. Gynecol.*, "Effects of Biorhythms on blood flow distribution in the pregnant uterus (Macaca Mulatta)", vol. 135, No. 7, pp. 828–840, Dec. 1, 1979.

Harbert, Jr., M. D., Guy M. et al., *Am. J. Obstet. Gynecol.*, "Biorhythms of the primate uterus (Macaca Mulatta) during labor and delivery", vol. 138, No. 6, pp. 666–695, Nov. 15, 1980.

Rhoads, G. G. et al. "Home Monitoring of Uterine Contractility . . . ", *Am. Journal of Obstet. Gynecol.* (1990) abstract.

ELECTRICAL IMPEDANCE IMAGING TO MONITOR MYOMETRIAL ACTIVITY

BACKGROUND OF THE INVENTION

The present invention relates in general to a non-invasive technique for monitoring myometrial activity in pregnant females.

A method of characterizing pregnant female myometrial activity to distinguish between contractions predictive of term or preterm labor and contractures which are not indicative of labor, is disclosed in U.S. Pat. No. 4,967,761 to Nathanielsz, which is hereby incorporated by reference. In this patent, discrete epochs of myometrial contractility are sensed, and signals representing these epochs are produced and stored. Characteristic repetitive frequencies of the signals are determined, which in turn can be used to determine whether the myometrial activity being characterized is predictive of term or preterm labor. The provision of such a technique is invaluable to physicians as an aid in predicting whether or not a pregnant female is going to give birth prematurely. Premature birth accounts for 75% of perinatal mortality and 50% of long-term neurological handicaps, and a major problem with management of preterm birth is the physician's inability to follow precisely the patterns of myometrial activity in pregnant women at risk.

The method disclosed in U.S. Pat. No. 4,967,761 is preferably implemented using either invasive or non-invasive sensors. The sensors can be used to measure electrical impulses, pressure, heat, chemical changes or deformation of the uterine profile caused by the myometrial contractility. The signals generated by the sensors are ultimately stored and analyzed or processed to determine the characteristic repetitive frequencies of the signals, the repetitive frequency being a characteristic of whether the myometrial activity is contractions predictive of term or preterm labor, sometimes referred to as Type I activity, or innocuous contractures, sometimes referred to as Type II activity.

In one invasive technique for obtaining these measurements, myometrial electrodes are implanted in experimental animals to obtain a precise, accurate registration of myometrial contractility continuously throughout pregnancy. Clearly, these methods are too invasive for use in pregnant women. The only known method used to register myometrial activity in pregnant women non-invasively employs a device known as an external tocodynamometer, which is essentially a strain gauge strapped to the abdomen of the pregnant women to register rounding of the uterus as it contracts. It has many disadvantages including relatively poor sensitivity and high susceptibility to movement artifact. It is also ineffective in women more than 160% ideal body weight because subcutaneous adipose tissue interferes with registration of the mechanical effects of myometrial contraction at the abdominal skin surface. This inability to use the external tocodynamometer in overweight women is a major restriction, since many of the women at risk for preterm labor are of this body shape, especially multiparous women. At a recent NIH conference, external tocodynamometry was carefully reviewed by research scientists, obstetricians, industrialists and NIH personnel. The shortcomings of the external tocodynamometer were noted at the conference, and the overall view was that there was a need for a better sensor mechanism. Although large amounts of money are currently being invested by commercial companies in attempts to improve the tocodynamometer, it appears clear that a new type of non-invasive myometrial activity monitoring system is needed.

SUMMARY OF THE INVENTION

It is therefore the object of the present invention to provide an improved non-invasive technique for monitoring myometrial activity, particularly uterine contractility.

This and other objects of the invention are achieved with a technique that employs electrical impedance imaging (EII), also known as applied potential tomography, as an indicator of uterine contractility. EII is a technique which involves the application of low amplitude, relatively low-frequency alternating currents through the body and reconstruction of images of spatial distribution of tissue resistivity from measurements of current or voltage on the surface of the body. This technique is disclosed in detail in U.S. Pat. No. 4,617,939 to Brown et al., which is also hereby incorporated by reference.

Differences in dielectric properties, represented by impedance or resistivity, among biological tissues at given frequencies enable interpretation of the data obtained using EII. Blood has a resistivity of 1.5 ohm-m compared with 27.2 ohm-m for fat and 166 ohm-m for bone at 50 kHz. It is known that when the myometrium contracts, uterine blood flow decreases. It is theorized that this change in blood flow produces the observed marked resistivity changes which can be sensed and employed to follow myometrial activity, particularly uterine contractility.

To obtain measurements for the EII technique, a plurality of skin electrodes is placed around the circumference of a pregnant female's abdomen, a short distance below the umbilicus. An alternating current is applied between an arbitrarily chosen drive pair of the electrodes, and the resulting potential difference between all adjacent pairs of electrodes is measured. This process is repeated using sequential pairs of the electrodes as the drive pair. By computing the integrated resistivity for periodic measurements across the abdomen or in a selected region of interest, such as the uterus, temporal changes in resistivity can be followed. These changes are correlated in a computer to changes in the magnitude of uterine contractility.

BRIEF DESCRIPTION OF THE DRAWINGS

The foregoing and additional objects, features and advantages of the present invention will become apparent from the following detailed description of a preferred embodiment thereof, taken in conjunction with the accompanying drawings, in which.

DETAILED DESCRIPTION OF THE PREFERRED EMBODIMENTS

Figure 1A:
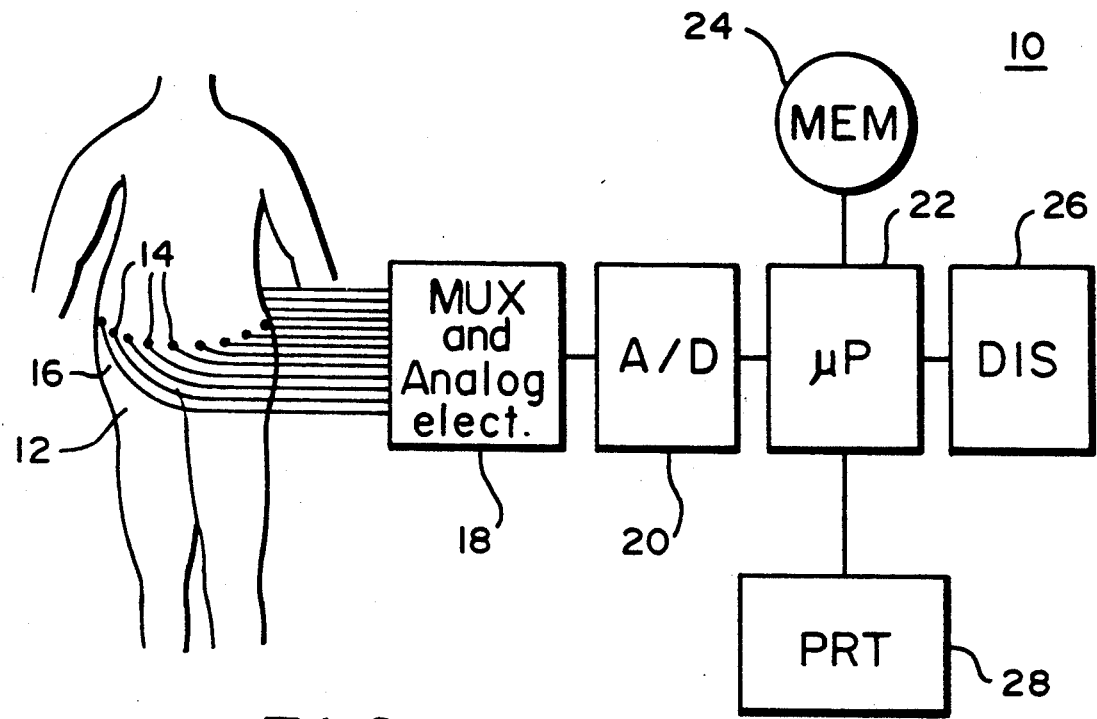
FIG. 1A is a block diagram showing an EII system for obtaining myometrial activity information from a pregnant female.
Figure 1B:
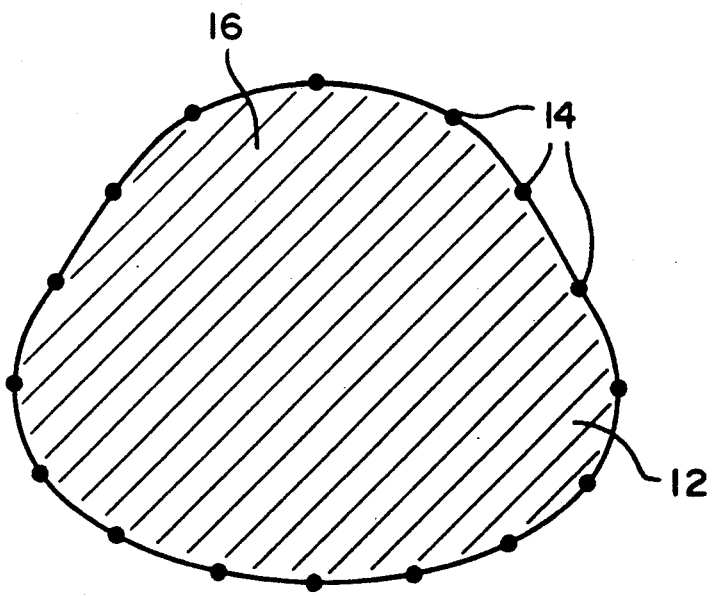
FIG. 1B is a diagrammatic cross section of a pregnant female illustrating electrode placement for the EII system of FIG. 1A.

Turning now to a more detailed consideration of a preferred embodiment of the present invention, FIG. 1A illustrates a conventional EII, or applied potential tomography, system 10 for measuring the integrated resistance of the abdominal tissues of a pregnant female 12. The system 10 is generally similar to that disclosed in U.S. Pat. No. 4,617,939 to Brown et al., and includes a plurality of spaced electrodes 14 which are disposed around the circumference of the female's abdomen indicated at 16 as illustrated best in FIG. 1B. Preferably, the system disclosed in Brown et al. employs 16 of the electrodes 14, although a larger number of electrodes, e.g. 32, can be employed to obtain even more precise measurements if desired. Electrical potentials are applied to pairs of the electrodes 14 in a sequential manner, while the remaining of the electrodes 14 generate signals in response thereto. Multiplexing and analog electronics indicated at 18 are provided for applying electrical potential between all adjacent electrodes 14 in turn, and recording potential differences between all other adjacent electrode pairs to provide a profile of peripheral potential gradient. The analog profile gradient is digitized by an A/D converter 20 and then fed to a microprocessor 22 where the data is either stored in a memory 24, or outputted to a display 26 or a printer 28.

The EII sensor system illustrated in FIG. 1A can be employed to monitor and measure the magnitude of uterine contractility non-invasively and accurately through measurement of integrated abdominal tissue resistance. In the operation of the EII system 10, low amplitude, relatively low-frequency (e.g. 1 mA or less at 50 KH$_2$) alternating currents are passed through the female 12 via an arbitrarily chosen drive pair of the electrodes 14, and the resulting potential difference is measured between all adjacent pairs of the remaining electrodes 14. This process is repeated using sequential pairs of the electrodes 14 as the drive pair. With the system disclosed in Brown et al., all of the potential difference measurements can be made in less than 1 ms and a complete data set for an image is collected in under 100 ms. The potential measurements enable the integrated resistivity across the abdomen or in a selected region of interest, such as the uterus, to be computed. By computing the integrated resistivity for repeated measurements, temporal changes in resistivity variations can be followed.

It has been established that when the myometrium contracts, uterine blood flow falls. Since EII of the abdominal tissues interrogated is affected by the amount of blood in the tissues, this blood flow variation may explain why EII measurements have been observed to be correlated to myometrial activity. Regardless of the exact reason why it works, the present invention provides an excellent method by which the magnitude of uterine contractility can be accurately monitored and measured non-invasively so that the onset of labor can be predicted early enough that measures can be taken to prevent it if it is premature.

Figure 2:
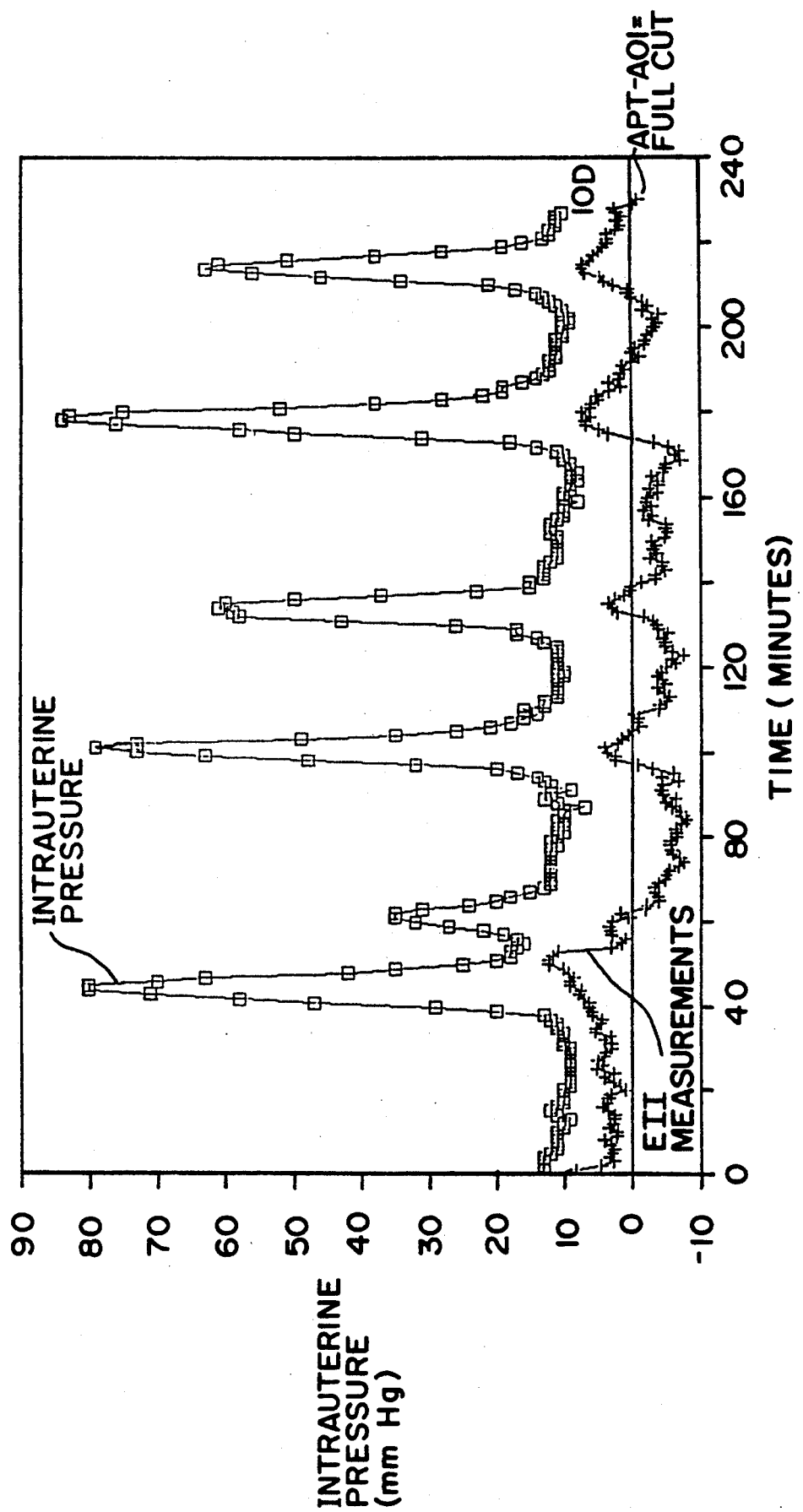
FIG. 2 is a graph comparing changes in intrauterine pressure with the output of a EII test system constructed in accordance with FIG. 1A.

Experiments have been conducted on three pregnant woman in labor to compare EII obtained results with results obtained by a known invasive technique for monitoring myometrial activity in which intrauterine pressure is recorded with an indwelling catheter. The results of these experiments are illustrated in the graph in FIG. 2. This graph shows the changes in uterine pressure by the curve connecting the squares and the output of the EII abdominal sensor by the curve connecting the plus signs. As illustrated, the correspondence between the two measurement techniques is very good. In practice, this can be made even better because this initial analysis interrogated the whole maternal abdomen, and with software programming, the abdomen can be divided into regions of interest to give better discrimination.

Although the invention has been disclosed in terms of a preferred embodiment, it will be understood that numerous variations and modifications could be made thereto without departing from the spirit and scope of the invention as set forth in the following claims.

What is claimed is:

1. A method of monitoring non-invasively pregnant female myometrial activity comprising the steps of:
   a) employing electrical impedance imaging to obtain integrated resistivity measurements of a pregnant female's abdominal tissues during periods of uterine contractility activity including contractions and contractives; and,
   b) determining from said obtained resistivity measurements, the relative magnitude of uterine contractility of said pregnant female during said measurements.

2. The method of claim 1 wherein the step of employing electrical impedance imaging comprises:
   i) applying a plurality of spaced electrodes to the abdomen of the pregnant female to be monitored;
   ii) passing an alternating current through said female by way of a pair of said electrodes;
   iii) measuring the resulting potential difference between all adjacent pairs of the remaining electrodes;
   iv) repeating steps (ii) and (iii) by applying alternating current to sequential pairs of said electrodes;
   v) computing the integrated resistivity across the abdomen of the female from all said potential difference measurements; and,
   vi) repeating steps (ii) through (v) periodically to obtain a plurality of integrated resistivity measurements.

3. The method of claim 1 further including the step of characterizing the myometrial activity from the determined contractility magnitude measurements to distinguish between myometrial activity predictive of term or preterm labor and that of innocuous contractures.

* * * * *

UNITED STATES PATENT AND TRADEMARK OFFICE
CERTIFICATE OF CORRECTION

PATENT NO. : 5,217,022
DATED : June 8, 1993
INVENTOR(S) : Peter W. Nathanielsz

It is certified that error appears in the above-indentified patent and that said Letters Patent is hereby corrected as shown below:

Column 4, Claim 1, line 1, "monitoring non-invasively" should be --non-invasively monitoring--; and, Column 4, Claim 1, line 32, "contractives" should be --contractures--.

Signed and Sealed this

Twenty-first Day of December, 1993

Attest:

BRUCE LEHMAN

*Attesting Officer*    *Commissioner of Patents and Trademarks*